United States Patent
Patch

(10) Patent No.: US 6,292,526 B1
(45) Date of Patent: Sep. 18, 2001

(54) METHODS AND APPARATUS FOR PREPROCESSING VOLUMETRIC COMPUTED TOMOGRAPHY DATA

(75) Inventor: Sarah K. Patch, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/428,103

(22) Filed: Oct. 27, 1999

(51) Int. Cl.$^7$ ........................................................ A61B 6/03
(52) U.S. Cl. ................................... 378/4; 378/15; 378/901
(58) Field of Search .................... 378/4, 15, 901

(56) References Cited

U.S. PATENT DOCUMENTS

| | | | |
|---|---|---|---|
| 5,390,111 | 2/1995 | Tam | 378/16 |
| 6,084,936 | 7/2000 | Patch | 378/4 |
| 6,173,030 | * 1/2001 | Patch | 378/4 |

OTHER PUBLICATIONS

A.A. Kirillov, Soviet Doklady On a Problem of I.M. Gelfand; (Translation), pp. 268–269.
Michael Defrise, et al., Sep. 2000, IEEE 2000, Fast and exact Fourier rebinning using John's equation (Because of the copyright date, this reference is not believed to be prior art).
Sigurdur Helgason, 1980, Progress in Mathematics The Radon Transform; pp. 1–75.
Fritz John, 1938, Duke Math Journal The Ultrahyperbolic Differential Equation With Four Independent Variables; pp. 300–322.
Duke Math Journal, vol. 9 An Explicit Formula for the Solution of the Ultrahyperbolic Equation in Four Independent Variables; pp. 272–282.
Glynn Owens, 1953, Duke Math Journal, vol. 20 A Boundary–Value Problem for Analytic Solutions of An Ultrahyperbolic Equation; pp. 29–38.
Hiroyuki Kudo, Frederic Noo, Michel Defrise, 1998, Phys. Med. Biol., vol. 43 Cone–beam Filtered–backprojection Algorithm for Truncated Helical Data; pp. 2885–2909.
Pierre Grangeat, 1991, Mathematical Methods in Tomography–Lecture Notes in Mathematics Mathematical Framework of Cone Beam 3D Reconstruction Via the First Derivative of the Radon Transform; pp. 66–97.
Heang K. Tuy, Jun. 1983, Siam J. Applied Math, vol. 43, No. 3, An Inversion Formula for Cone–beam Reconstruction; pp. 546–552.
Michel Defrise, Xuan Liu, 1999, Inverse Problems, vol. 15 A Fast Rebinning Algorithm for 3D PositronEmission Tomography Using John's Equation; pp. 1047–1065.
A.A. Kirillov, Soviet Doklady On a Problem of I.M. Gelfand; (Translation not available), pp. 268–269.

* cited by examiner

Primary Examiner—David V. Bruce
(74) Attorney, Agent, or Firm—Armstrong Teasdale LLP; Christian G. Cabou

(57) ABSTRACT

The present invention is in one embodiment a method of processing projection data collected in a helical scan performed along a helical trajectory relative to an object being scanned. The method includes steps of defining a coordinate system to parameterize the data and generating estimates of projection data not on the helical trajectory by solving ultrahyperbolic equations in the defined coordinate system.

30 Claims, 3 Drawing Sheets

METHODS AND APPARATUS FOR PREPROCESSING VOLUMETRIC COMPUTED TOMOGRAPHY DATA

BACKGROUND OF THE INVENTION

This invention relates generally to computed tomography and, more particularly, to reconstructing an image using data collected in a scan using a computed tomography system.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Cone beam scanning is performed using a multi-dimensional detector array instead of a linear detector array as is used in a fan beam scan. In a cone beam helical scan, the x-ray source and the multi-dimensional detector array are rotated with a gantry within the imaging plane as the patient is moved in the z-axis synchronously with the rotation of the gantry. Such a system generates a multi-dimensional helix of projection data.

Currently, 3D reconstruction algorithms are necessary to perform high quality image reconstruction from volumetric computed tomograph (VCT) data. One known algorithm for performing image reconstruction using data collected in a cone beam scan is sometimes referred to as the Feldkamp (FDK) algorithm. FDK is an approximate algorithm. When the cone angle is zero, FDK reduces to filtered back projection in 2D and is exact. However, FDK's image quality decreases with increasing cone angle. Exact algorithms for helical VCT data are sometimes referred to as Radon Based Techniques. However, Radon techniques are always slow and sometimes unstable.

BRIEF SUMMARY OF THE INVENTION

There is therefore provided, in one embodiment of the present invention a method of processing projection data collected in a helical scan performed along a helical trajectory relative to an object being scanned. The method includes steps of defining a coordinate system to parameterize the data and generating estimates of projection data not on the helical trajectory by solving ultrahyperbolic equations in the defined coordinate system.

The above described preprocessing provides the advantage that focal spot positions for which views are computed can be chosen to minimize reconstruction time. For example, if a physician prefers to view particular slices of an object, only focal spot positions within those planes need be determined and images reconstructed for that data.

DETAILED DESCRIPTION OF THE INVENTION

Although the present invention is sometimes described herein in the context of medical imaging, the present invention can be used in many other contexts including, for example, in the inspection of industrial components. The present invention is not limited to use in medical imaging.

Figure 1:
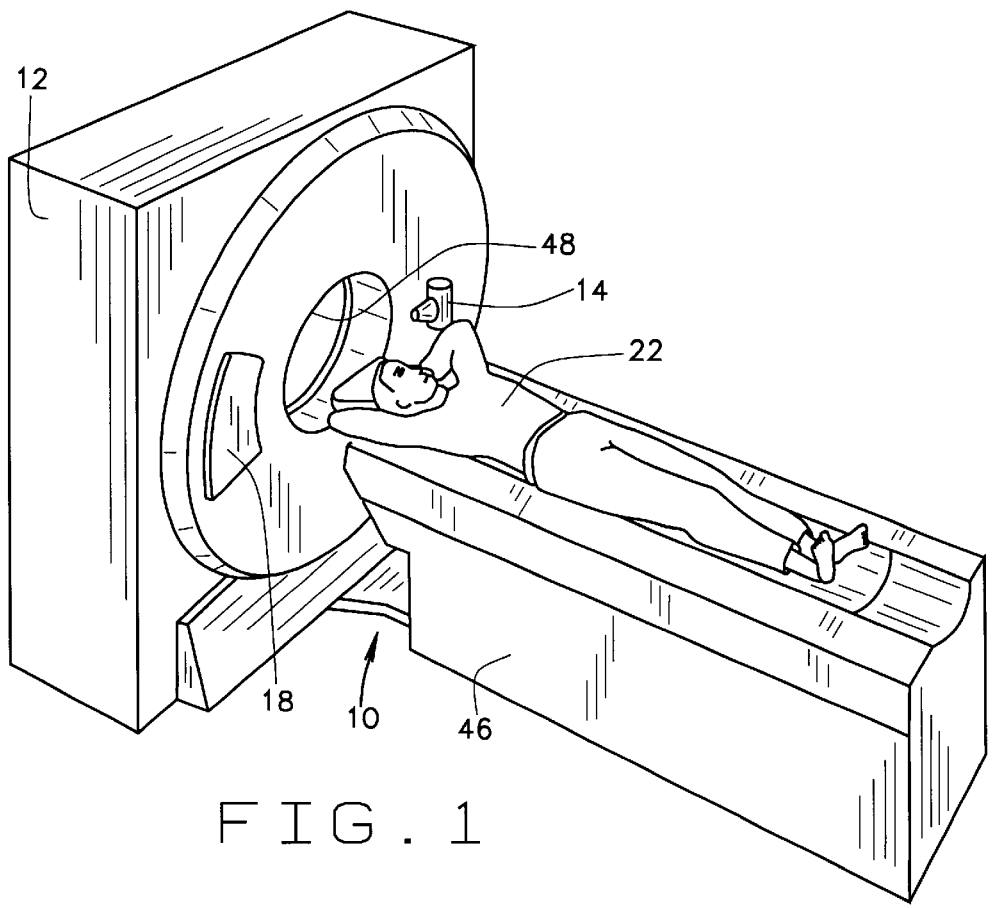
FIG. 1 is a pictorial view of a CT imaging system.
Figure 2:
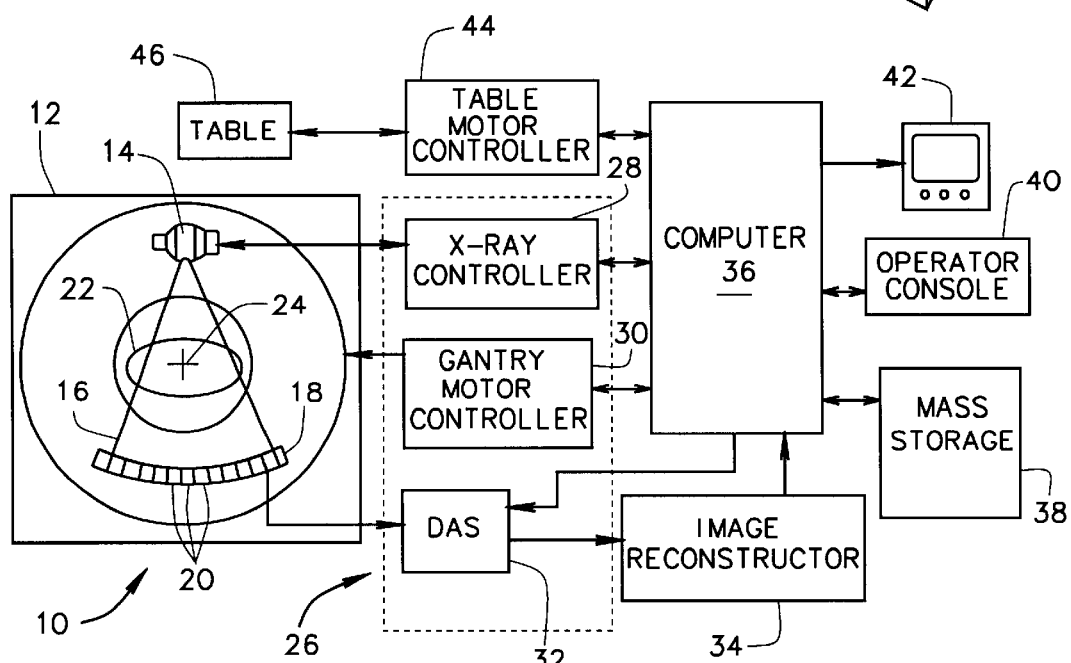
FIG. 2 is a block schematic diagram of the system illustrated in FIG. 1.

Referring specifically to the drawings, FIGS. 1 and 2 illustrate a computed tomograph (CT) imaging system 10 including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 is a multidimensional array, and each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38. The algorithms described below may be performed by a processor in image reconstructor 34. Such algorithms, however, may be performed by computer 36, or by another processor coupled to the system.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Generally, and in one aspect, the present invention relates to providing a mathematically exact technique for computing unmeasured volumetric computed tomography (VCT) from measured data. Specifically, preprocessing volumetric computed tomography (VCT) data corresponding to a helical source trajectory so that unmeasured views corresponding to focal spot (FS) positions not on the helix are computed in the Fourier domain from Fourier components of measured views. The computed data can then be used in exact reconstruction algorithms such as 2D filtered back-projection or 3D Fourier reconstructions. An advantage of performing many 2D filtered back-projection reconstructions on many computed axial data sets is that existing algorithms and existing reconstruction hardware and software can be used. Fourier reconstructions are much faster computationally because the time consuming back-projection step is avoided. Both 2D filtered back-projection and 3D Fourier reconstructions provide mathematically exact reconstructions. To decrease total reconstruction time with minimal loss of image quality, VCT views can be computed on intertwining helixes.

Fourier components of unmeasured views are computed from Fourier components of measured data by solving a characteristic boundary value problem for John's partial differential equation (PDE) using measured VCT data as boundary values. Rather than differentiate CT data directly, the Fourier transform of the CT data is differentiated. Solving the PDE in the Fourier domain converts the PDE to a family of ordinary differential equations. Since VCT projections are real-valued, their Fourier transforms are Hermitian symmetric, and the number of computations are reduced in half. Since the Fourier transform of a bounded object is smooth, derivatives in the Fourier domain are accurately approximated numerically. Because the Fourier transform preserves $L^2$ norms, the method is stable in $L^2$. The present invention is particularly suitable for generating images having large regions of interest (ROI).

Figure 3:
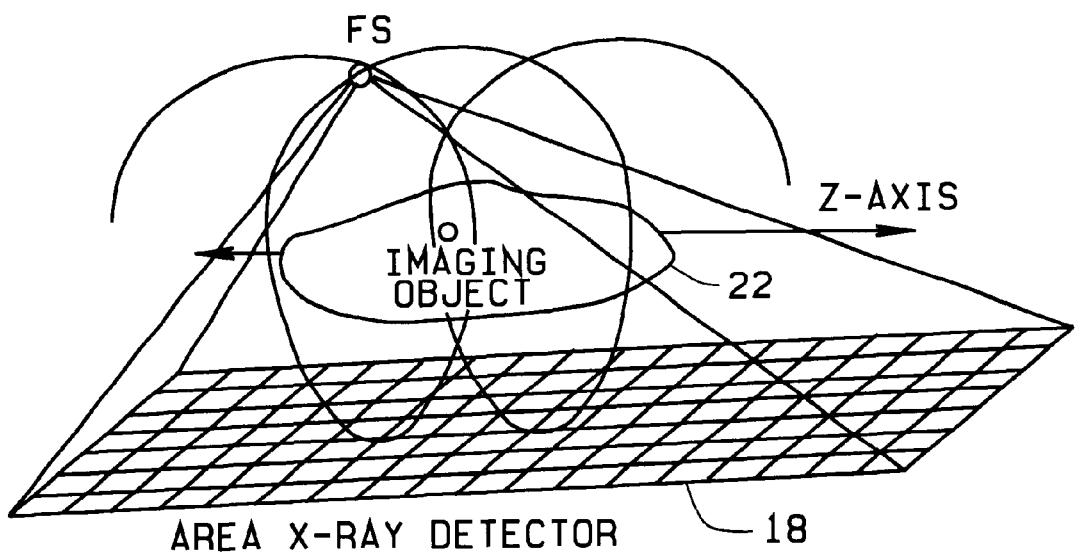
FIG. 3 illustrates a helical source trajectory around an imaging object.

FIG. 3 illustrates a trajectory T of the focal spot (FS) around an object, e.g., patient 22. X-ray source 14 and detector array 18 are rotated around object 22 along helical trajectory T to collect projection data. The present invention provides the advantage that FS positions for which views are computed can be chosen to minimize reconstruction time. For example, if a physician prefers to view particular slices of an object, only FS positions within those planes need be determined and images reconstructed for that data.

More specifically, volumetric computed tomography (VCT) data is subject to range conditions as described, for example, in John, *Duke Journal of Mathematics*, 1938. These range conditions are far stronger than the range conditions upon two-dimensional computed tomography data and require that VCT data satisfy the ultrahyperbolic partial differential equations:

$$\left(\frac{\partial^2}{\partial \eta_i \partial \xi_j} - \frac{\partial^2}{\partial \eta_j \partial \xi_i}\right) u(\xi; \eta) = 0 \tag{0.1}$$

for $i, j = 1, 2, 3$

Figure 4:
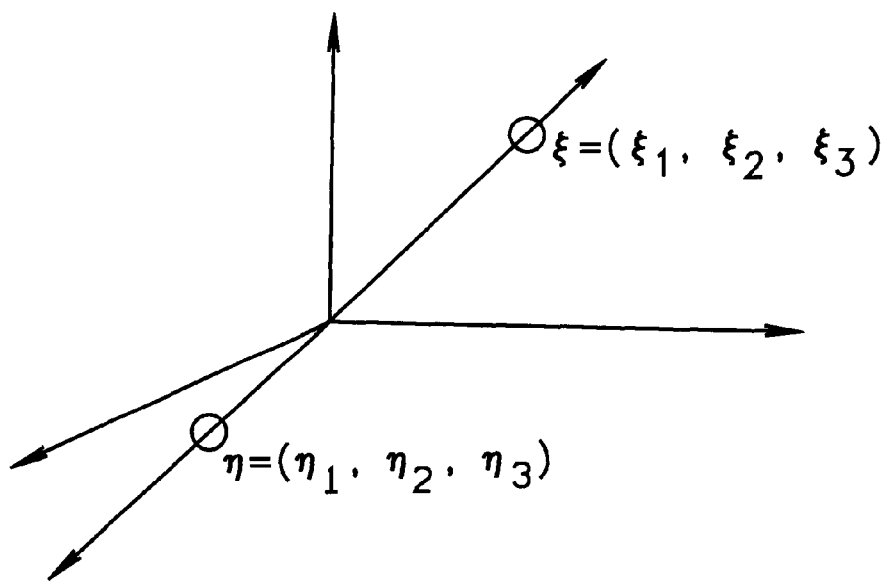
FIG. 4 illustrates a line that integrates ρ, linear attenuation coefficients (LAC) of an imaging object, through points ξ and η.

The space of lines in $\mathbf{R}$ is four dimensional, although six parameters are often used to characterize lines in $\mathbf{R}$, as shown in FIG. 4.

Normalized CT data measures line integrals of the three dimensional imaging object's linear attenuation coefficient (LAC). The map taking the LAC to its set of line integrals is underdetermined, and the inversion of a function is line integrals to the function itself is overdetermined. This overdetermination manifests itself in the fact that a function is line integrals must satisfy equation (0.1). The present invention enforces the range conditions upon VCT data by solving the characteristic boundary value problem for the ultrahyperbolic equations where the boundary value data is collected by a third generation helical CT system with a flat panel x-ray detector.

More specifically, the coordinates are changed to parameterize third generation data and rewriting the ultrahyperbolic differential equations (0.1) in the new coordinate system. When the FS and detector array radii of rotation about the central axis are fixed, as is the case for third generation systems, one of the ultrahyperbolic equations is trivially satisfied and the other two reduce to the same partial differential equation.

With respect to John's equation, and for simplicity of notation:

$$u(\xi; \eta) = \int_{IR} f(\eta + t(\xi - \eta)) dt \tag{0.2}$$

$$= \frac{X_{N\rho}(\xi_1 \xi_2 \xi_3; \eta_1 \eta_2 \eta_3)}{\sqrt{(\xi_1 - \eta_1)^2 + (\xi_2 + \eta_2)^2 + (\xi_3 + \eta_3)^2}}$$

where $X_{N\rho}(\xi, \eta)$ denotes normalized line integrals of $\rho$, the linear attenuation coefficients (LAC) of the imaging object, along the line through the points $\xi$ and $\eta$.

To enforce consistency conditions upon third generation VCT data, $\xi$ and $\eta$ are written in terms of third generation parameterization. Assume that $\xi$ is the FS position and that $\eta$ is the point of intersection of the line with the x-ray detector. For a third generation system, the focal spot travels along a helical trajectory about the z axis. The detector also rotates about the z-axis directly opposite from the FS. In order to solve John's equation for the boundary value data, lines through the object are reparameterized so that in the new coordinate system, it will be easy to solve. In a third generation system, the FS lies on the cylinder $\sqrt{\xi_1^2 + \xi_2^2} = R$ and the detector lies directly opposite the FS at a distance D from the z-axis. Therefore:

$\xi_1 = \rho \cos \theta$ $\xi_2 = \rho \sin \theta$ $\xi_2 = z$ $\eta_1 = -d \cos \theta - \alpha_1 \sin \theta$ $\eta_2 = -d \sin \theta - \alpha_1 \cos \theta$ $\eta_3 = z + \alpha_2$ where $\rho$ and $d$ are the rotation distances of the FS and detector array from the z-axis, respectively, $\alpha_1$ and $\alpha_2$ are the coordinates in the plane of the x-ray detector, z is distance along the z axis, and θ is the rotation angle within the x-ray plane. Nonzero derivatives of the third generation coordinates with respect to the original Cartesian coordinates are written below.

$$\frac{\partial \theta}{\partial \xi_1} = \frac{-\sin\theta}{\rho} \quad \frac{\partial d}{\partial \xi_1} = \frac{\alpha_1 \sin\theta}{\rho}$$

$$\frac{\partial \theta}{\partial \xi_2} = \frac{\cos\theta}{\rho} \quad \frac{\partial d}{\partial \xi_2} = \frac{\alpha_1 \cos\theta}{\rho}$$

$$\frac{\partial \rho}{\partial \xi_1} = \cos\theta \quad \frac{\partial d}{\partial \eta_1} = -\cos\theta$$

$$\frac{\partial \rho}{\partial \xi_2} = \sin\theta \quad \frac{\partial d}{\partial \eta_2} = -\sin\theta$$

$$\frac{\partial z}{\partial \xi_1} = 1$$

$$\frac{\partial \alpha_1}{\partial \xi_1} = \frac{-d\sin\theta}{\rho} \quad \frac{\partial \alpha_1}{\partial \xi_2} = \frac{d\cos\theta}{\rho}$$

$$\frac{\partial \alpha_1}{\partial \eta_1} = \frac{-\sin\theta}{\rho} \quad \frac{\partial \alpha_1}{\partial \eta_2} = \frac{\cos\theta}{\rho}$$

$$\frac{\partial \alpha_2}{\partial \xi_3} = 1 \quad \frac{\partial \alpha_2}{\partial \eta_3} = -1$$

By simply applying the chain rule, the partial derivatives with respect to the Cartesian variables, $\xi_i$ and $\eta_j$ are:

$$\frac{\partial}{\partial \xi_1} = \frac{\partial \rho}{\partial \xi_1}\frac{\partial}{\partial \rho} + \frac{\partial \theta}{\partial \xi_1}\frac{\partial}{\partial \theta} + \frac{\partial z}{\partial \xi_1}\frac{\partial}{\partial z} + \tag{0.4}$$

$$\frac{\partial d}{\partial \xi_1}\frac{\partial}{\partial d} + \frac{\partial \alpha_1}{\partial \xi_1}\frac{\partial}{\partial \alpha_1} + \frac{\partial \alpha_2}{\partial \xi_1}\frac{\partial}{\partial \alpha_2}$$

$$= \cos\theta\frac{\partial}{\partial \rho} - \frac{\sin\theta}{\rho}\frac{\partial}{\partial \theta} + 0 + \frac{\alpha_1 \sin\theta}{\rho}\frac{\partial}{\partial d} +$$

$$\frac{-d\sin\theta}{\rho}\frac{\partial}{\partial \alpha_1} + 0$$

$$= \cos\theta\frac{\partial}{\partial \rho} - \frac{\sin\theta}{\rho}\left(\frac{\partial}{\partial \theta} - \alpha_1\frac{\partial}{\partial d} + d\frac{\partial}{\partial \alpha_1}\right)$$

Similarly, $$\frac{\partial}{\partial \xi_2} = \sin\theta\frac{\partial}{\partial \rho} + \frac{\cos\theta}{\rho}\left(\frac{\partial}{\partial \theta} - \alpha_1\frac{\partial}{\partial d} + d\frac{\partial}{\partial \alpha_1}\right) \tag{0.5}$$

$$\frac{\partial}{\partial \xi_3} = \frac{\partial}{\partial z} - \frac{\partial}{\partial \alpha_2}$$

$$\frac{\partial}{\partial \eta_1} = -\left(\cos\theta\frac{\partial}{\partial d} + \frac{\sin\theta}{\rho}\frac{\partial}{\partial \alpha_1}\right)$$

$$\frac{\partial}{\partial \eta_2} = -\left(\sin\theta\frac{\partial}{\partial d} - \frac{\cos\theta}{\rho}\frac{\partial}{\partial \alpha_1}\right)$$

$$\frac{\partial}{\partial \eta_3} = \frac{\partial}{\partial \alpha_2}$$

To simplify notation define the differential operators, P and Q:

$$P = \left(\frac{\partial}{\partial \theta} - \alpha_1\frac{\partial}{\partial d} + d\frac{\partial}{\partial \alpha_1}\right) \tag{0.6}$$

$$Q = \left(\frac{\partial}{\partial z} - \frac{\partial}{\partial \alpha_2}\right) \tag{0.7}$$

and write the ultrahyperbolic equations in terms of the third generation coordinates:

$$0 = \left(\frac{\partial^2}{\partial \eta_1 \partial \xi_2} - \frac{\partial^2}{\partial \eta_2 \partial \xi_1}\right) u(\xi; \eta) \tag{0.8}$$

$$= -\left(\cos\theta\frac{\partial}{\partial d} + \sin\theta\frac{\partial}{\partial \alpha_1}\right)\left[\sin\theta\frac{\partial}{\partial \rho} + \frac{\cos\theta}{\rho}P\right] -$$

$$\left(-\sin\theta\frac{\partial}{\partial d} + \cos\theta\frac{\partial}{\partial \alpha_1}\right)\left[\cos\theta\frac{\partial}{\partial \rho} - \frac{\sin\theta}{\rho}P\right]$$

$$= -\left[\frac{1}{\rho}\frac{\partial P}{\partial d} + \frac{\partial^2}{\partial \alpha_1 \partial \rho}\right] u(p, \theta, z, \alpha_1, \alpha_2, d)$$

$$0 = \left(\frac{\partial^2}{\partial \eta_1 \partial \xi_3} - \frac{\partial^2}{\partial \eta_3 \partial \xi_1}\right) u(\xi; \eta) \tag{0.9}$$

$$-\left(\cos\theta\frac{\partial}{\partial d} + \sin\theta\frac{\partial}{\partial \alpha_1}\right)\left(\frac{\partial}{\partial z} - \frac{\partial}{\partial \alpha_1}\right) -$$

$$\frac{\partial}{\partial \alpha_2}\left[\cos\theta\frac{\partial}{\partial \rho} - \frac{\sin\theta}{\rho}P\right]$$

$$= \left(-\cos\theta\frac{\partial}{\partial d}\left(\frac{\partial}{\partial z} - \frac{\partial}{\partial \alpha_2}\right) - \cos\theta\frac{\partial^2}{\partial \alpha_2 \partial \rho} +$$

$$\sin\theta\frac{\alpha_1}{\rho}\frac{\partial^2}{\partial \alpha_2 \partial d}\right] + \sin\theta\left[\left(1 + \frac{d}{\rho}\right)\frac{\partial^2}{\partial \alpha_2 \partial \alpha_1} -$$

$$\frac{\partial^2}{\partial \alpha_1 \partial z} + \frac{1}{\rho}\frac{\partial^2}{\partial \alpha_2 \partial \theta}\right] u(\rho, \theta, z, \alpha_1, \alpha_2, d)$$

$$= \left(\sin\theta\left[\frac{-\alpha_1}{\rho}\frac{\partial^2}{\partial \alpha_2 \partial d} + \left(1 + \frac{d}{\rho}\right)\frac{\partial^2}{\partial \alpha_2 \partial \alpha_1} -$$

$$\frac{\partial^2}{\partial \alpha_1 \partial z} + \frac{1}{\rho}\frac{\partial^2}{\partial \alpha_2 \partial \theta}\right] -$$

$$\cos\theta\left[Q\frac{\partial}{\partial d} + \frac{\partial^2}{\partial \alpha_2 \partial \rho}\right]\right) u(\rho, \theta, z, \alpha_1, \alpha_2, d)$$

$$= \left(\sin\theta\left[\frac{1}{\rho}\frac{\partial}{\partial \alpha_2}P - \frac{\partial}{\partial \alpha_1}Q\right] - \cos\theta\left[Q\frac{\partial}{\partial d} + \frac{\partial^2}{\partial \alpha_2 \partial \rho}\right]\right)$$

$$u(\rho, \theta, z, \alpha_1, \alpha_2, d)$$

Similarly, $$0 = \left(\frac{\partial^2}{\partial \eta_2 \partial \xi_3} + \frac{\partial^2}{\partial \eta_3 \partial \xi_2}\right) u(\xi; \eta) \tag{0.10}$$

$$= \left(\cos\theta\left[\frac{1}{\rho}\frac{\partial}{\partial \alpha_2}P - \frac{\partial}{\partial \alpha_1}Q\right] +$$

$$\sin\theta\left[Q\frac{\partial}{\partial d} + \frac{\partial^2}{\partial \alpha_2 \partial \rho}\right]\right) u(p, \theta, z, \alpha_1, \alpha_2, d)$$

There are common factors in equations 0.9 and 0.10. Assuming that the order of differentiation can be switched with respect to any two variables, the differential operators are defined as:

$$L_1 = \left[\frac{1}{\rho}\frac{\partial P}{\partial d} + \frac{\partial^2}{\partial \alpha_1 \partial \rho}\right]$$

$$L_2 = \left[Q\frac{\partial}{\partial d} + \frac{\partial^2}{\partial \alpha_2 \partial \rho}\right]$$

$$L_3 = \left[\frac{1}{\rho}\frac{\partial P}{\partial \alpha_2} - \frac{\partial Q}{\partial \alpha_1}\right]$$

For $\ominus = (\cos\theta, \sin\theta)$, then equations 0.8, 0.9, and 0.10 become:

$$0 = L_1 u \tag{0.11}$$

$$0 = \Theta(L_2 u, L_3 u) \tag{0.12}$$

$$0 = \Theta^\perp \cdot (L_2 u, L_3 u) \tag{0.13}$$

which implies $$L_1 u = 0 \quad (0.14)$$

$$L_2 u = 0 \quad (0.15)$$

$$L_3 u = 0 \quad (0.16)$$

In a third generation system, the radii are fixed at $\rho \equiv 0.541$ m($=R$) and d$\equiv 0.408$ m($=D$). Therefore, u is measured for fixed values of $\rho$ and d, but for varying $\theta$, z, $\alpha_1$, and $\alpha_2$. The measured data presents line integrals of a function defined in $R^3$ and therefore should be a function of three independent variables. However it is a function of four variables, subject to the conditions in equation 0.16. In order for the dimension count to be correct, equation 0.16 must give only one independent constraint upon u. This can be seen by writing equation 0.16 modulo first order identities on u.

Using the definition of u in equation 0.2 and defining L as the line through the points $\xi$ and $\rho$, then for density functions $f$:

$$(\xi - \eta) \cdot \nabla_\xi u(\xi, \eta) = (\xi - \eta) \cdot \nabla \int_R f(\eta + t(\xi - \eta)) dt$$

$$= \int_R (\xi - \eta) \cdot \nabla_\xi f(\eta + t(\xi - \eta)) dt$$

$$= \int_R t(\xi - \eta) \cdot \nabla f(\eta + t(\xi - \eta)) dt$$

$$= \int_L t \frac{df}{dt} dt, \text{ integrate by parts to get}$$

$$= tf \Big|_{L_{-\infty}}^{L_{+\infty}} - \int_L f dt \text{ so,}$$

Therefore, $$(\xi - \eta) \cdot \nabla_\xi u(\xi, \eta) = -u(\xi, \eta) \quad (0.17)$$

Similarly, $$(\xi - \eta) \cdot \nabla_\eta u(\xi, \eta) = u(\xi, \eta) \quad (0.18)$$

Recall that $\Theta = (\cos \theta, \sin \theta)$, and using equations 0.4 and 0.5, and rewriting the equations with respect to third generation variables:

$$(\xi - \eta) \cdot \nabla_\xi u(\xi, \eta) = ((\rho + d)\Theta - \alpha_1 \Theta^{195}; \alpha_2) \cdot \quad (0.19)$$

$$\left(\Theta \frac{\partial}{\partial \rho} + \frac{1}{\rho} \Theta^\perp \left(\frac{\partial}{\partial \theta} - \alpha_1 \frac{\partial}{\partial d} + d \frac{\partial}{\partial \alpha_1}\right); \frac{\partial}{\partial z} - \frac{\partial}{\partial \alpha_2}\right) u = \quad (0.20)$$

$$(\rho + d) \frac{\partial}{\partial \rho} - \frac{\alpha_1}{\rho} \left(\frac{\partial}{\partial \theta} - \alpha_1 \frac{\partial}{\partial d} + d \frac{\partial}{\partial \alpha_1}\right) - \alpha_2 \left(\frac{\partial}{\partial z} - \frac{\partial}{\partial \alpha_2}\right)$$

In a third generation geometry, and by equating equation 0.17 with equation 0.19 and equating equation 0.18 with equation 0.20, then $\partial / \partial d$ and $\partial / \partial \rho$ can be expressed in terms of z, $\theta$, $\alpha_1$ and $\alpha_2$ and their partials.

$$\frac{\partial u}{\partial d} = \frac{-1}{\rho + d} \left(I + \alpha_1 \frac{\partial}{\partial \alpha_1} + \alpha_2 \frac{\partial}{\partial \alpha_2}\right) u \quad (0.21)$$

$$\frac{\partial u}{\partial \rho} = \frac{1}{\rho + d} \left(-I + \frac{\alpha_1}{\rho} P + \alpha_2 Q\right) u \quad (0.22)$$

The equivalence of $L_2$ and $L_3$ can then be readily shown.

$$L_2 u = \left[Q \frac{\partial}{\partial d} + \frac{\partial^2}{\partial \alpha_2 \partial \rho}\right] \quad (0.23)$$

$$= \frac{1}{\rho + d} \left[-Q\left(I + \alpha_1 \frac{\partial}{\partial \alpha_1} + \alpha_2 \frac{\partial}{\partial \alpha_2}\right) u - \frac{\partial}{\partial \alpha_2} \left(-I + \frac{\alpha_1}{\rho} P + \alpha_2 Q\right) u\right]$$

$$= \frac{-1}{\rho + d} [Qu + \alpha_1 Q u_{\alpha_1} + \alpha_2 Q u_{\alpha_2} - u_{\alpha_2}) -$$

$$\left(-u_{\alpha_2} + \frac{\alpha_1}{\rho} \frac{\partial P}{\partial \alpha_2} + Qu + \alpha_2 Q u_{\alpha_2}\right)]$$

$$= \frac{-\alpha_1}{\rho + d} \left[-Q u_{\alpha_1} + \frac{1}{\rho} \frac{\partial P}{\partial \alpha_2}\right]$$

$$= \frac{-\alpha_1}{\rho + d} \left[-\frac{\partial Q u}{\partial \alpha_1} + \frac{1}{\rho} \frac{\partial P u}{\partial \alpha_2}\right]$$

$$= \frac{\alpha_1}{\rho + d} L_3 u$$

Similarly, $L_1$ is equivalent to $L_2$ and $L_3$. Therefore, there is only one differential consistency condition upon third generation cone beam data. Expanding in terms of the four variables $\alpha_1$, $\alpha_2$, z, and $\theta$, then:

$$0 = \frac{\partial P u}{\partial \alpha_2} - \rho \frac{\partial Q u}{\partial \alpha_1} \quad (0.24)$$

$$= \left[\frac{\partial}{\partial \alpha_2}\left(\frac{\partial}{\partial \theta} - \alpha_1 \frac{\partial}{\partial d} + d \frac{\partial}{\partial \alpha_1}\right) - \rho \frac{\partial}{\partial \alpha_1}\left(\frac{\partial}{\partial z} - \frac{\partial}{\partial \alpha_2}\right)\right] u$$

$$= \left[\frac{\partial}{\partial \alpha_2}\left(\frac{\partial}{\partial \theta} + \frac{\alpha_1}{\rho + d}\left(I + \alpha_1 \frac{\partial}{\partial \alpha_1} + \alpha_2 \frac{\partial}{\partial \alpha_2}\right) + d \frac{\partial}{\partial \alpha_1}\right) - \rho \frac{\partial}{\partial \alpha_1}\left(\frac{\partial}{\partial z} - \frac{\partial}{\partial \alpha_2}\right)\right] u \text{ which implies}$$

$$\frac{\partial^2 u}{\partial \alpha_2 \partial \theta} - \rho \frac{\partial^2 u}{\partial z \partial \alpha_1} = -\frac{2\alpha_1}{(\rho + d)} \frac{\partial u}{\partial \alpha_2} - \frac{\alpha_1 \alpha_2}{\rho + d} \frac{\partial^2 u}{\partial \alpha_2^2} - \quad (0.25)$$

$$\left[(\rho + d) + \frac{\alpha_1^2}{(\rho + d)}\right] \frac{\partial^2 u}{\partial \alpha_2 \partial \alpha_1}$$

The left hand side of equation 0.25 is first order with respect to z and $\theta$.

Standard numerical methods, including finite elements and finite difference schemes, well known in numerical analysis, solve the characteristic boundary value problem for u at all ( z, $\theta$) from measurements of u for ( z, $\theta$) on a helical source trajectory. The trajectory may either be of continuously varying pitch and/or piecewise constant pitch.

In order to verify equation 0.25, equation 0.2 is re-written in third generation coordinates as:

$$u(\rho, \theta, z, d, \alpha_1 \alpha_2) = \int_{IR} f(\rho \Theta - t(\rho + d)\Theta + t \alpha_1 \Theta^\perp; z + t \alpha_2) dt \quad (0.26)$$

Also, $$\frac{df}{dt} = \quad (0.27)$$

$$(-(\rho + d)\Theta + \alpha_1 \Theta^\perp; \alpha_2) \cdot \nabla_{x,y,z} f(\rho \Theta - t(\rho + d)\Theta + t \alpha_1 \Theta^\perp; z + t \alpha_2)$$

Partials of u can be determined as:

$$u_z = \int_{IR} f_z(\rho\Theta - t(\rho + d)\Theta + t\alpha_1\Theta^\perp; z + t\alpha_2)dt \quad (0.28)$$

$$u_{\alpha_2} = \int_{IR} tf_z(\rho\Theta - t(\rho + d)\Theta + t\alpha_1\Theta^\perp; z + t\alpha_2)dt$$

$$u_{z,\alpha_1} = \int_{IR} t\Theta^\perp \cdot \nabla_{x,y} f_z dt$$

$$u_{\alpha_2,\alpha_1} = \int_{IR} t^2\Theta^\perp \cdot \nabla_{x,y} f_z dt$$

$$u_{\alpha_2,\alpha_2} = \int_{IR} t^2 f_{z,z} dt$$

$$u_{\alpha_2,\theta} = \int_{IR} t[\rho\Theta^\perp - t(\rho + d)\Theta^\perp - t\alpha_1\Theta] \cdot \nabla_{x,y} f_z dt$$

Using these values in equation 0.25 provides:

$$0 = \int_{IR} \left( t[(\rho - t(\rho + d))\Theta^\perp - t\alpha_1\Theta] - \rho t\Theta^\perp + \right. \quad (0.29)$$

$$\left[(\rho + d) + \frac{\alpha_1^2}{(\rho + d)}\right] t^2 \Theta^\perp \right) \cdot \nabla_{x,y} f_z +$$

$$\frac{2\alpha_1}{(\rho + d)} tf_z + \frac{\alpha_1\alpha_2}{\rho + d} t^2 f_{z,z} dt$$

$$= \frac{\alpha_1}{(\rho + d)} \int_{IR} [t^2(-(\rho + d)\Theta + \alpha_1\Theta^\perp; \alpha_2) \cdot$$

$$\nabla_{x,y,z} f_z + 2tf_z] dt$$

$$= \frac{\alpha_1}{(\rho + d)} \int_{IR} \frac{d}{dt}(t^2 f) dt$$

$$= (t^2 f)\Big|_{t = -\infty}^{t = \infty}$$

$$= 0 - 0$$

because $f$ has compact support.

Although standard numerical solvers for partial differential equations such as equation 0.25 can be used subject to the boundary condition that u is measured $\forall \alpha_1, \alpha_2$ and $z=p\theta$, it is also possible to transform it into a system of ordinary differential equations. $u \in C_0$ is bounded and for each $(\theta, z)$ pair, has compact support in $\alpha_1$, and $\alpha_2$. u is measured along a path $z=p\theta$, $\alpha_1, \alpha_2 \in R$. The left hand side of equation 0.25 is first order with respect to z and θ.

Since u has compact support in $\alpha_1, \alpha_2$, its Fourier transform with respect to $\alpha_1, \alpha_2$, is smooth. By taking the Fourier transform of equation 0.25 with respect to $\alpha_1$, and $\alpha_2$ where $\kappa_1$ and $\kappa_2$, are dual variables of $\alpha_1$, and $\alpha_2$ then:

$$\pi i(\kappa_2, -R\kappa_1) \cdot (\hat{u}_\theta, \hat{u}_z) = \quad (0.30)$$

$$\frac{\kappa_2}{R + D}\left(2\hat{u}_{\kappa_1} - \kappa_2\hat{u}_{\kappa_1\kappa_2} + \kappa_1\left(\pi^2(R + D)^2\hat{u} - \hat{u}_{\kappa_1\kappa_2}\right)\right)$$

more simply written, for each fixed $(\kappa_1, \kappa_2)$ pair $$\frac{d\hat{u}}{ds} = g(\hat{u}, \hat{u}_{\kappa_1}, \hat{u}_{\kappa_1\kappa_2}, \hat{u}_{\kappa_1\kappa_1}) \quad (0.31)$$

where $$\frac{d\hat{u}}{ds}$$

is the derivative of u in the direction $(\kappa_2, -R\kappa_1)$.

The arguments of g are all smooth functions. Multiple application of standard ordinary differential equation solvers, such as Runge-Kutta, can be used to solve equation 0.31 subject to the boundary conditions provided by measurements corresponding to a helical source trajectory providing complete data. One example of such boundary conditions is when u is measured along the source trajectory $z=p\theta, \forall \alpha_1, \alpha_2$.

Figure 5:
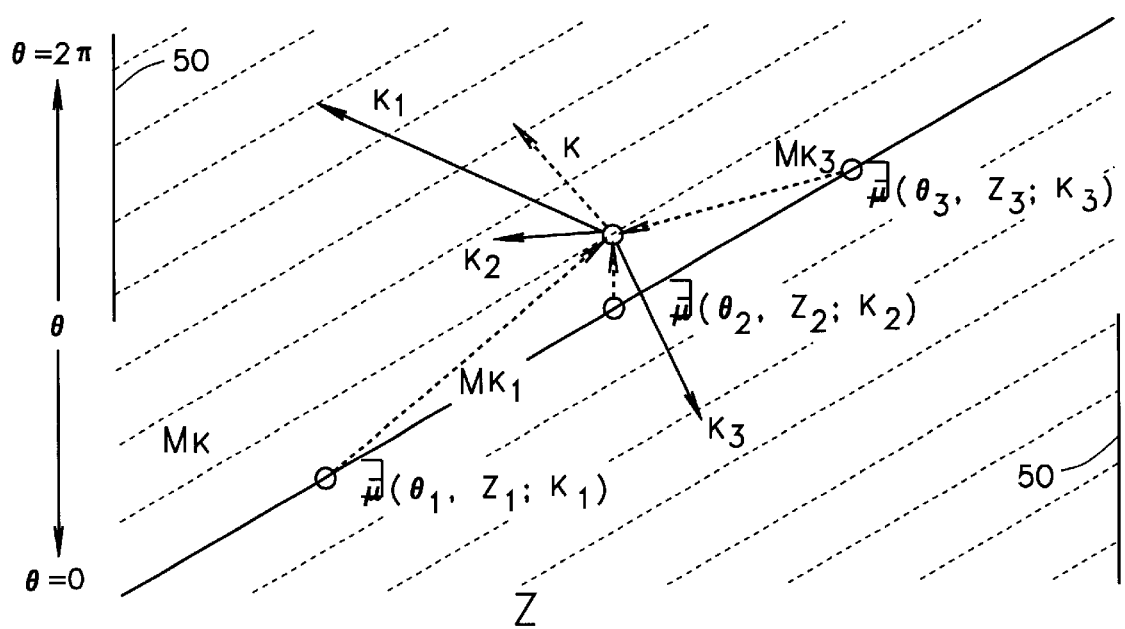
FIG. 5 illustrates a focal spot position that has Fourier parameters determined by solving an ordinary differential equation from a directional derivative in direction Mκ.

Equation (0.30) clarifies conditions required for a complete data set. A measured data set is complete if for each FS position represented by (θ, z) and for each $(\kappa_1, \kappa_2)$ pair in the Fourier domain, the vector starting at (θ, z) and pointing in direction $(\kappa_2, -R \kappa_1)$ intersects its source trajectory. One example of a source trajectory measuring complete data is shown in FIG. 5. In this case Fourier components for computed views are determined by solving ODE from a directional derivative in direction Mκ, where M is a matrix. ODEs are coupled in that the Foruier information is required as initial conditions for all FS on positions on helix (shown in FIG. 3) as well as one view from half scan axial data, measured by FS positions 50. Conversely, each measured view influences Fourier components of all unmeasured views. Component κ is inaccessible because Mκ parallels the source trajectory. As shown in FIG. 5, the helical pitch is piecewise constant, first p=0, then p=150, and finally p=0. In other words, axial scans immediately precede and follow a single helical rotation.

The hyperbolic partial differential equation can be solved in the spatial or Fourier domain and is well posed for band-limited VCT data. X-ray detectors integrate a signal across each pixel's surface area, effectively bandlimiting VCT measurements. Therefore any consistent and stable numerical solver can solve the resultant equation.

While the invention has been described in terms of various specific embodiments, those skilled in the art will recognize that the invention can be practiced with modification within the spirit and scope of the claims.

What is claimed is:

1. A method for processing projection data collected in a helical scan performed using an x-ray source and an area detector that travel along a helical trajectory relative to an object being scanned, said method comprising the steps of:

defining a coordinate system to parameterize the data; and generating estimates of projection data not on the helical trajectory by solving ultrahyperbolic equations in the defined coordinate system.

2. A method in accordance with claim 1 wherein data are processed in the Fourier domain and the partial differential equation $$\pi i(\kappa_2, -R\kappa_1) \cdot (\hat{u}_\theta, \hat{u}_z) = \frac{\kappa_2}{R + D}\left(2\hat{u}_{\kappa_1} - \kappa_2\hat{u}_{\kappa_1\kappa_2} + \kappa_1\left(\pi^2(R + D)^2\hat{u} - \hat{u}_{\kappa_1\kappa_2}\right)\right)$$

is converted to a family of ordinary differential equations of the form:

$$\frac{d\hat{u}}{ds} = g(\hat{u}, \hat{u}_{\kappa_1}, \hat{u}_{\kappa_1,\kappa_2}, \hat{u}_{\kappa_1,\kappa_1})$$

where $$\frac{d\hat{u}}{ds}$$

is a derivative of u in a direction $(\kappa_2, -R\kappa_1)$.

3. A method in accordance with claim 2 wherein arguments of the function g are smooth functions, and wherein multiple applications of standard ODE solvers are used to solve the equation.

4. A method in accordance with claim 3 wherein a Runge-Kutta numerical method is used to solve the equation.

5. A method in accordance with claim 3 wherein the equation is solved subject to a boundary condition that u is measured along the source trajectory $z=p\theta, \forall \alpha_1, \alpha_2$.

6. A method in accordance with claim 2 wherein:

$$\frac{\partial^2 u}{\partial \alpha_2 \partial \theta} - \rho \frac{\partial^2 u}{\partial z \partial \alpha_1} = -\frac{2\alpha_1}{(\rho+d)} \frac{\partial u}{\partial \alpha_2} - \frac{\alpha_1 \alpha_2}{\rho+d} \frac{\partial^2 u}{\partial \alpha_2^2} - \left[(\rho+d) + \frac{\alpha_1^2}{(\rho+d)}\right] \frac{\partial^2 u}{\partial \alpha_2 \partial \alpha_1}.$$

7. A method according to claim 1 wherein the data are collected in a helical scan of piecewise constant pitch.

8. A method according to claim 1 wherein the data are collected in a helical scan of continually varying pitch.

9. A method according to claim 1 wherein the data are processed by solving a boundary value problem for partial differential equations $$\left(\frac{\partial^2}{\partial \eta_i \partial \xi_j} - \frac{\partial^2}{\partial \eta_j \partial \xi_i}\right) u(\xi; \eta) = 0 \quad \text{for } i, j = 1, 2, 3$$

modulo the identities $(\xi-\eta) \cdot \nabla_\xi u(\xi;\eta) = -u(\xi;\eta)$ and $(\xi-\eta) \cdot \nabla_\eta u(\xi;\eta) = u(\xi;\eta)$ using normalized measured projections as boundary values.

10. A method according to claim 1 wherein the data are processed by solving a boundary value problem for partial differential equations $$\left(\frac{\partial^2}{\partial \eta_i \partial \xi_j} - \frac{\partial^2}{\partial \eta_j \partial \xi_i}\right) u(\xi; \eta) = 0 \quad \text{for } i, j = 1, 2, 3$$

modulo the identities $(\xi-\eta) \cdot \nabla_\xi u(\xi;\eta) = -u(\xi;\eta)$ and $(\xi-\eta) \cdot \nabla_\eta u(\xi;\eta) = u(\xi;\eta)$ in the Fourier domain and using Fourier transforms of normalized measured projections as boundary values.

11. A method according to claim 1 wherein the data are processed in the spatial domain by solving a boundary value problem for partial differential equation $$\left(\frac{\partial^2}{\partial \eta_i \partial \xi_j} - \frac{\partial^2}{\partial \eta_j \partial \xi_i}\right) u(\xi; \eta) = 0 \quad \text{for } i, j = 1, 2, 3$$

using a standard finite difference numerical scheme for partial differential equations using normalized measured projections as boundary values.

12. A method according to claim 11 wherein Fourier transforms of normalized scan data are Hermitian symmetric.

13. A method according to claim 1 wherein the data are processed in the spatial domain by solving a boundary value problem for partial differential equation $$\pi i(\kappa_2, -R\kappa_1) \cdot (\hat{u}_\theta, \hat{u}_z) = \frac{\kappa_2}{R+D}\left(2\hat{u}_{\kappa_1} - \kappa_2 \hat{u}_{\kappa_1 \kappa_2} + \kappa_1\left(\pi^2(R+D)^2 \hat{u} - \hat{u}_{\kappa_1 \kappa_2}\right)\right)$$

using a standard finite element numerical scheme for partial differential equations using the normalized measured projections as boundary values.

14. A method according to claim 1 wherein the data are processed in the Fourier domain by solving a boundary value problem for partial differential equation $$\pi i(\kappa_2, -R\kappa_1) \cdot (\hat{u}_\theta, \hat{u}_z) = \frac{\kappa_2}{R+D}\left(2\hat{u}_{\kappa_1} - \kappa_2 \hat{u}_{\kappa_1 \kappa_2} + \kappa_1\left(\pi^2(R+D)^2 \hat{u} - \hat{u}_{\kappa_1 \kappa_2}\right)\right)$$

using a standard finite difference numerical scheme for partial differential equations using the Fourier transform of normalized measured projections as boundary values.

15. A method according to claim 14 wherein Fourier transforms of normalized scan data are Hermitian symmetric.

16. A method according to claim 1 wherein the data are processed in the Fourier domain by solving a boundary value problem for partial differential equation $$\pi i(\kappa_2, -R\kappa_1) \cdot (\hat{u}_\theta, \hat{u}_z) = \frac{\kappa_2}{R+D}\left(2\hat{u}_{\kappa_1} - \kappa_2 \hat{u}_{\kappa_1 \kappa_2} + \kappa_1\left(\pi^2(R+D)^2 \hat{u} - \hat{u}_{\kappa_1 \kappa_2}\right)\right)$$

using a standard finite elements numerical scheme for partial differential equations using the Fourier transform of normalized measured projections as boundary values.

17. A method according to claim 16 wherein Fourier transforms of normalized scan data are Hermitian symmetric.

18. A computed tomography (CT) imaging system for generating an image of an object, said imaging system including at least one x-ray detector array and at least one x-ray source projecting an x-ray beam, said imaging system configured to:

collect projection data in a helical scan where the x-ray source and the detector array travel along a helical trajectory relative to the object being scanned;

define a coordinate system to parameterize the data; and generate estimates of projection data not on the helical trajectory by solving ultrahyperbolic equations in the defined coordinate system.

19. A system according to claim 18 further configured to generate estimates of projection data by solving characteristic boundary problems for:

$$\pi i(\kappa_2, -R\kappa_1) \cdot (\hat{u}_\theta, \hat{u}_z) = \frac{\kappa_2}{R+D}\left(2\hat{u}_{\kappa_1} - \kappa_2 \hat{u}_{\kappa_1 \kappa_2} + \kappa_1\left(\pi^2(R+D)^2 \hat{u} - \hat{u}_{\kappa_1 \kappa_2}\right)\right)$$

equivalently, a family of ordinary differential equations of the form:

$$\frac{d\hat{u}}{ds} = g(\hat{u}, \hat{u}_{\kappa_1}, \hat{u}_{\kappa_1,\kappa_2}, \hat{u}_{\kappa_1,\kappa_1})$$

where $$\frac{d\hat{u}}{ds}$$

is a derivative of u in a direction $(\kappa_2, -R\kappa_1)$.

20. A system according to claim 19 further configured to apply standard ordinary differential equation solvers to solve the equation wherein arguments of the function g are smooth functions.

21. A system according to claim 20 further configured to apply a Runge-Kutta numerical method to solve the equation.

22. A system according to claim 19 further configured to solve the equation subject to a boundary condition that u is measured along the source trajectory $z=p\theta, \forall \alpha_1, \alpha_2$.

23. A system according to claim 18 further configured such that:

$$\frac{\partial^2 u}{\partial \alpha_2 \partial \theta} - \rho \frac{\partial^2 u}{\partial z \partial \alpha_1} = -\frac{2\alpha_1}{(\rho+d)} \frac{\partial u}{\partial \alpha_2} - \frac{\alpha_1 \alpha_2}{\rho+d} \frac{\partial^2 u}{\partial \alpha_2^2} - \left[(\rho+d) + \frac{\alpha_1^2}{(\rho+d)}\right] \frac{\partial^2 u}{\partial \alpha_2 \partial \alpha_1}.$$

24. A system according to claim 18 further configured to collect data in a helical scan of piecewise constant pitch.

25. A system according to claim 18 further configured to collect data in a helical scan of continually varying pitch.

26. A system according to claim 18 further configured to process data by solving partial differential equations $$\left(\frac{\partial^2}{\partial \eta_i \partial \xi_j} - \frac{\partial^2}{\partial \eta_j \partial \xi_i}\right) u(\xi; \eta) = 0 \quad \text{for } i, j = 1, 2, 3$$

modulo the identities $(\xi-\eta) \cdot \nabla_{86} u(\xi;\eta) = -u(\xi;\eta)$ and $(\xi-\eta) \cdot \nabla_\eta u(\xi;\eta) = u(\xi;\eta)$ using normalized measured projections as boundary values.

27. A system according to claim 18 further configured to process the data in the spatial domain by solving a partial differential equation $$\left(\frac{\partial^2}{\partial \eta_i \partial \xi_j} - \frac{\partial^2}{\partial \eta_j \partial \xi_i}\right) u(\xi; \eta) = 0 \quad \text{for } i, j = 1, 2, 3$$

using a standard finite difference numerical scheme for partial differential equations using the normalized measured projections as boundary values.

28. A system according to claim 18 further configured to process the data in the spatial domain by solving a partial differential equation $$\left(\frac{\partial^2}{\partial \eta_i \partial \xi_j} - \frac{\partial^2}{\partial \eta_j \partial \xi_i}\right) u(\xi; \eta) = 0 \quad \text{for } i, j = 1, 2, 3$$

using a standard finite element numerical scheme for partial differential equations using the normalized measured projections as boundary values.

29. A method according to claim 18 further configured to process the data in the Fourier domain by solving a partial differential equation $$\pi i (\kappa_2, -R\kappa_1) \cdot (\hat{u}_\theta, \hat{u}_z) = \frac{\kappa_2}{R+D} \left(2 \hat{u}_{\kappa_1} - \kappa_2 \hat{u}_{\kappa_1 \kappa_2} + \kappa_1 \left(\pi^2 (R+D)^2 \hat{u} - \hat{u}_{\kappa_1 \kappa_2}\right)\right)$$

using a standard finite difference numerical scheme for partial differential equations using the Fourier transform of normalized measured projections as boundary values.

30. A method according to claim 18 further configured to process the data in the Fourier domain by solving a partial differential equation $$\pi i (\kappa_2, -R\kappa_1) \cdot (\hat{u}_\theta, \hat{u}_z) = \frac{\kappa_2}{R+D} \left(2 \hat{u}_{\kappa_1} - \kappa_2 \hat{u}_{\kappa_1 \kappa_2} + \kappa_1 \left(\pi^2 (R+D)^2 \hat{u} - \hat{u}_{\kappa_1 \kappa_2}\right)\right)$$

using a standard finite elements numerical scheme for partial differential equations using the Fourier transform of normalized measured projections as boundary values.

* * * * *

UNITED STATES PATENT AND TRADEMARK OFFICE
CERTIFICATE OF CORRECTION

PATENT NO. : 6,292,526 B1
DATED : September 18, 2001
INVENTOR(S) : Sarah K. Patch It is certified that error appears in the above-identified patent and that said Letters Patent is hereby corrected as shown below:

Column 4,
Line 24, delete "rewriting" and insert therefor -- rewrite --.
Line 38, equation (0.2), delete "$(\xi_2+\eta_2)^2 + (\xi_3+\eta_3)^2$" and insert therefor -- $\xi_2-\eta_2)^2 + (\xi_3-\eta_3)^2$ --.

Line 53, delete " $\sqrt{\xi_{1^2}+\xi_{2_2}}$ " and insert therefor -- $\sqrt{\xi_1^2 + \xi_2^2}$ --.

Line 56, at right-margin to indicate equation(s) number insert therefor -- (0.3) --.

Column 5,
Line 7, delete "p" and insert therefor -- $\rho$ --.

Column 6,
Line 14, equation (0.9), before "-(cos" insert therefor -- = --.

Line 14, equation (0.9), delete " $-\dfrac{\partial}{\partial \alpha_1}$ " and insert therefor -- $-\dfrac{\partial}{\partial \alpha_2}$ --.

Line 18, equation (0.9), between "=(" and "-cos$\theta$" insert therefor -- [ --.
Line 39, equation (0.10), delete "+" and insert therefor -- - --.
Line 65, equation (0.12), between "$\Theta$" and "(L$_2$" insert therefor -- · --.

Column 7,
Lines 24, 39, 43 and 48, delete "($\xi$, $\eta$)" (shown 6 times) and insert therefor -- ($\xi$; $\eta$) --.
Line 48, delete "$\Theta^{195}$" and insert therefor -- $\Theta^\perp$ --.

Column 12,
Line 5, delete equation shown and insert therefor

-- $-\left(\dfrac{\partial^2}{\partial \eta_i \partial \xi_j} - \dfrac{\partial^2}{\partial \eta_j \partial \xi_i}\right) u(\xi;\eta) = 0$    for i, j = 1, 2, 3 --.

UNITED STATES PATENT AND TRADEMARK OFFICE
CERTIFICATE OF CORRECTION

PATENT NO. : 6,292,526 B1
DATED : September 18, 2001
INVENTOR(S) : Sarah K. Patch It is certified that error appears in the above-identified patent and that said Letters Patent is hereby corrected as shown below:

Column 13,
Line 38, delete "$_{86}u$" and insert therefor -- $_\zeta u$ --.

Signed and Sealed this

Twelfth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,292,526 B1
DATED : September 18, 2001
INVENTOR(S) : Sarah K. Patch It is certified that error appears in the above-identified patent and that said Letters Patent is hereby corrected as shown below:

Column 4,
Line 24, delete "rewriting" and insert therefor -- rewrite --.
Line 38, equation (0.2), delete "$(\xi_2+\eta_2)^2 + (\xi_3+\eta_3)^2$" and insert therefor
-- $(\xi_2-\eta_2)^2 + (\xi_3-\eta_3)^2$ --.

Line 53, delete " $\sqrt{\xi_{1^2}+\xi_{22}}$ " and insert therefor -- $\sqrt{\xi_1^2 + \xi_2^2}$ --.

Line 56, at right-margin to indicate equation(s) number insert therefor -- (0.3) --.

Column 5,
Line 7, delete "p" and insert therefor -- $\rho$ --.

Column 6,
Line 14, equation (0.9), before "-(cos" insert therefor -- = --.
Line 18, equation (0.9), between "=(" and "-cos$\theta$" insert therefor -- [ --.
Line 39, equation (0.10), delete "+" and insert therefor -- - --.
Line 65, equation (0.12), between "$\Theta$" and "($L_2$" insert therefor -- · --.

Column 7,
Lines 24, 39, 43 and 48, delete "($\xi$, $\eta$)" (shown 6 times) and insert therefor
-- ($\xi$; $\eta$) --.
Line 48, delete "$\Theta^{195}$" and insert therefor -- $\Theta^\perp$ --.

Column 12,
Line 5, delete equation shown and insert therefor

-- $\left(\dfrac{\partial^2}{\partial\eta_i\partial\xi_j} - \dfrac{\partial^2}{\partial\eta_j\partial\xi_i}\right)u(\xi;\eta) = 0$   for i, j = 1, 2, 3 --.

UNITED STATES PATENT AND TRADEMARK OFFICE
CERTIFICATE OF CORRECTION

PATENT NO. : 6,292,526 B1
DATED : September 18, 2001
INVENTOR(S) : Sarah K. Patch It is certified that error appears in the above-identified patent and that said Letters Patent is hereby corrected as shown below:

<u>Column 13,</u>
Line 38, delete "$_{86}u$" and insert therefor -- $_{\xi}u$ --.

This certificate suprsedes Certificate of Correction issued August 12, 2003.

Signed and Sealed this

Twenty-fifth Day of May, 2004

JON W. DUDAS
*Acting Director of the United States Patent and Trademark Office*